United States Patent [19]

Haffer et al.

[11] Patent Number: 5,569,661
[45] Date of Patent: Oct. 29, 1996

[54] PROCESS FOR THE PRODUCTION OF B-CARBOLINES

[75] Inventors: Gregor Haffer; Klaus Nickisch, both of Berlin, Germany

[73] Assignee: Schering Aktiengesellschaft, Berlin, Germany

[21] Appl. No.: 436,414
[22] PCT Filed: Nov. 22, 1993
[86] PCT No.: PCT/DE93/01116
 § 371 Date: Jun. 23, 1995
 § 102(e) Date: Jun. 23, 1995
[87] PCT Pub. No.: WO94/12498
 PCT Pub. Date: Jun. 9, 1994

[30] Foreign Application Priority Data

Nov. 24, 1992 [DE] Germany ............ 42 40 672.2

[51] Int. Cl.⁶ .................. A61K 31/44; C07D 221/06
[52] U.S. Cl. .................. 514/292; 546/85; 546/87
[58] Field of Search ............... 514/292; 546/85, 546/87

[56] References Cited

U.S. PATENT DOCUMENTS 4,778,800 10/1988 Huth .................... 514/292

OTHER PUBLICATIONS

Vader et al Tetrahedron 1989, 45(17), 5595–610.

*Primary Examiner*—C. Warren Ivy
*Assistant Examiner*—Garth M. Dahlen
*Attorney, Agent, or Firm*—Millen, White, Zelano, & Branigan, P.C.

[57] ABSTRACT

A new process for the production of β-carbolines by dehydrogenation of tetrahydro-β-carbolines with trichloroisocyanuric acid is described.

1 Claim, No Drawings

PROCESS FOR THE PRODUCTION OF B-CARBOLINES

This is the national stage application of PCT/DE93/01116 filed Nov. 22, 1993.

The invention relates to a new process for the production of β-carbolines by dehydrogenation of tetrahydro-β-carbolines with trichloroisocyanuric acid.

On the basis of their affinity to the benzodiazepine receptors, β-carbolines show effects on the central nervous system and are suitable for the production of pharmaceutical agents. The industrial-scale production of β-carbolines in operation therefore has met with great interest recently. The synthesis of active ingredients is performed with several stages, and the yields are influenced in the individual stages by the purity of the starting product. Thus it is known, for example, from EP-239667 that β-carbolines can be produced over 3 stages, and an aromatization of the C-ring is performed in the last stage. The 1,2,3,4-tetrahydro-β-carbolines or their 1-carboxylic acid derivatives used as starting products for the dehydrogenation are isolated and, according to EP-190 987, reacted with tert-butyl hypochlorite in the presence of bases. Tert-butyl hypochlorite is poorly suited for industrial-scale syntheses, since it can decompose exothermally in chloromethane and acetone at elevated temperature and with the effect of light. Not only the potential of danger but also the poor dosability of tert-butyl hypochlorite require its replacement in industrial-scale syntheses. It is therefore desirable to develop a process for the production of β-carbolines which does not require the working-up of intermediate stages and makes possible the industrial-scale production of compounds with easily accessible and easily storable substances.

Surprisingly, it has now been found that in the dehydrogenation of tetrahydro-β-carbolines with trichloroisocyanuric acid, which occurs in very good yields, a working-up and isolation of the intermediate products is not necessary. The process according to the invention makes possible that β-carbolines starting from pseudo-gramine derivatives and Schiff bases can be produced in a one-pot reaction. Another advantage of the process according to the invention consists in the fact that trichloroisocyanuric acid is stable in storage and easily dosable as solid and the water-soluble reaction products can be separated easily in the working-up of the reaction mixture with aqueous bases.

The invention relates to the process for the production of compounds of formula I

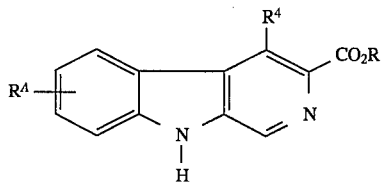

in which $R^A$ means hydrogen halogen, —$CHR^1$—$R^2$; phenyl, hetaryl or $OR^5$ optionally substituted with halogen, $C_{1-4}$ alkoxy or amino and can be single to double, and $R^1$ means hydrogen or $C_{1-4}$ alkyl, $R^2$ means hydrogen, $C_{1-4}$ alkyl, —O—$C_{1-4}$ alkyl or an optionally substituted phenyl, benzyl or phenoxy radical, and $R^5$ means hydrogen, $C_{1-6}$ alkyl, $C_{3-7}$ cycloalkyl or an optionally substituted phenyl, benzyl, hetaryl or benzocondensed hetaryl radical, $R^4$ means hydrogen, $C_{1-4}$ alkyl or $C_{1-4}$ alkoxy-$C_{1-2}$ alkyl and R means $C_{1-6}$ alkyl, characterized in that a compound of formula II

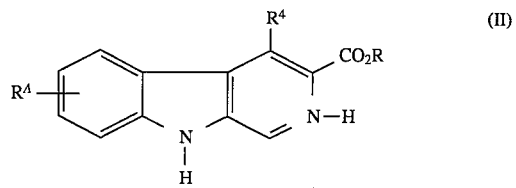

in which

R, $R^A$ and $R^4$ have the above meaning, is aromatized with trichloroisocyanuric acid in the presence of bases. Substituent $R^A$ can be in the A-ring in position 5–8, preferably in 5-, 6- or 7-position.

In each case, alkyl contains both straight-chain and branched-chain radicals, such as, for example, methyl, ethyl, propyl, isopropyl, butyl, isobutyl, sec-butyl, tert-butyl, pentyl, isopentyl and hexyl.

In each case, cycloalkyl can stand for cyclopropyl, cyclobutyl, cyclopentyl, cyclohexyl, cycloheptyl and 2methyl-cyclopropyl, and 3–5 carbon atoms are preferred.

If $R^5$ or $R^A$ means a hetaryl radical, the latter is 5- or 6-membered and contains 1–3 heteroatoms, such as nitrogen, oxygen and/or sulfur. For example, the following 5- and 6-ring heteroaromatic compounds can be mentioned: pyridine, pyrimidine, pyrazine, pyridazine, furan, thiophene, pyrrole, thiazole, imidazole, triazine.

If $R^5$ means a benzo-condensed hetaryl radical, the latter preferably contains 1–2 nitrogen atoms, such as quinoline, isoquinoline, quinoxaline or benzimidazole.

The substituent of the phenyl, benzyl, hetaryl and benzocondensed hetaryl radical $R^5$ can be single to triple in any position. Suitable substituents are halogens, nitro, cyano, $C_{1-4}$ alkyl, $C_{1-4}$ alkoxy, amino, $C_{1-4}$ alkoxycarbonyl, $C_{1-4}$ alkylthio and trifluoromethyl, and the single to double substitution with halogen is preferred for the phenyl and benzyl radical.

Halogen is to be understood to mean respectively fluorine, chlorine, bromine or iodine.

As preferred hetaryl radical and benzo-condensed hetaryl radicals $R^5$, nitrogen-containing heterocycles are possible, which optionally are substituted once to twice with halogen, $C_{1-4}$ alkyl, $C_{1-4}$ alkoxy or trifluoromethyl, especially with halogen.

As substituents of the phenyl, benzyl and phenoxy radical $R^2$, the substituents of the aromatic compounds mentioned for $R^5$ are suitable, especially halogens such as chlorine and bromine.

The reaction according to the invention takes place in inert aprotic solvents, such as hydrocarbons, halogenated hydrocarbons, cyclic or acyclic ethers and esters, such as, for example, toluene, benzene, xylene, hexane, methylene chloride, chloroform, dichloroethane, carbon tetrachloride, diethyl ether, dimethoxymethane, methyl-tert-butyl ether, isopropyl acetate, ethyl acetate, dimethylformamide.

As bases, all organic bases are suitable, especially tertiary amines, such as triethylamine, ethyldiisopropylamine, pyridine, 1,5-diazabicyclo-[4,3,0]-non-5-ene (DBN), 1,8-diazabicyclo[5,4,0]-undec-7-ene (DBU) and dimethylaminopyridine (DMAP).

The trichloroisocyanuric acid used according to the invention is added in equivalent amounts or in slight excess relative to the chlorine. In general, 0.7–0.9 molar equivalents of trichloroisocyanuric acid are added.

The reaction is performed at temperatures of –20° C. up to room temperature, and the reaction time can be shortened by heating the reaction mixture.

For working-up the reaction mixture, it is mixed with water and the precipitated compounds of formula I are separated.

The compounds produced according to the process of the invention are themselves valuable pharmaceutical agents or can be used as intermediate compounds for the production of active ingredients.

The production of the starting compounds is known or can be performed according to known processes or processes described here. For example, the production of pseudogramines is described in WO 91/16304.

EXAMPLE 1

A. Production of 2-(4-methoxybenzylidine-amino)-acetic acid isopropyl ester 35.9 ml of 4-methoxybenzaldehyde is dissolved under nitrogen and with stirring in 37.0 ml of dimethylformamide. After adding 53.8 ml of triethylamine and 21.0 g of magnesium sulfate, it is heated to +35° C. internal temperature, 45.38 g of glycine isopropyl ester hydrochloride dissolved in 150 ml of dimethylformamide is instilled in this solution within 30 minutes. It is stirred for 75 more minutes at +35° C. internal temperature. After cooling to +3°to +5° C. internal temperature, it is stirred for 60 more minutes, magnesium sulfate and triethylamine hydrochloride are suctioned off. The residue is rewashed in portions with a total of 110 ml of dimethylformamide.

B. Condensation of the Schiff Base of Glycine Ester with N-[1 -(4-benzyloxy-indolyl-3-yl)-2-methoxyethyl]-N-isopropylamine-(4-benzyloxypseudo-gramine)

Filtrate A is mixed with 51.0 g of potassium carbonate. With heating, 110 ml of solvent is distilled off in a vacuum. Under a weak nitrogen stream, it is heated under normal pressure to an internal temperature of 90°–110° C. In this connection, a solution of 50.0 g of 4-benzyloxypseudo-gramine in 295.0 ml of dimethylformamide is instilled within 60 minutes. It is stirred for 90 more minutes at +100°–110° C. internal temperature. After cooling to room temperature, the solid is filtered off and rewashed with 110.0 ml of dimethylformamide.

The filtrate is mixed at an internal temperature of +20°–25° C. with 150.0 ml of water and acidified with about 52 ml of semiconcentrated hydrochloric acid to pH 2.

Within 30 minutes, 11.02 ml of 37% aqueous formaldehyde solution dissolved in 137.0 ml of water at an internal temperature of +25° C. is instilled. After two more hours of stirring, it is allowed to stand overnight at room temperature.

The solution is mixed with 665.0 ml of water and extracted with 550 ml of toluene. Then, 1100.0 ml of toluene is added, heated to +30° to 35° C. and mixed in portions with 41 g of sodium bicarbonate. The toluene phase is washed with 550 ml of water and dried on sodium sulfate. The filtrate is concentrated by evaporation in a vacuum at a bath temperature of +40° C. to a volume of 665 ml.

The toluene solution is mixed with 45.3 ml of triethylamine and cooled to −15° C. internal temperature. A solution of 22.89 g of trichloroisocyanuric acid in 635.0 ml of isopropyl acetate is instilled ice-cooled within 20 minutes in toluene solution, in this case the internal temperature rises to −8° C. After 5 more minutes of stirring, 55.7 ml of triethylamine is added and stirred for 3 hours at room temperature. After standing overnight, 500 ml of water is instilled with vigorous stirring. After 30 minutes of stirring, the precipitate is suctioned off, washed with water and dried at +40° C. in a vacuum on potassium hydroxide. The organic phase is concentrated by evaporation to a volume of 100 ml, mixed with 2 ml of triethylamine and left to crystallization overnight. 41.8 g of 5-benzyloxy- 4-methoxymethyl-β-carboline-3-carboxylic acid-isopropyl ester of melting point 209° C. (69.95% of theory) is obtained.

EXAMPLE 2

Analogously to Example 1, 39.80 g (66.60% of theory) of 6-benzyloxy-4-methoxymethyl-β-carboline-3-carboxylic acid isopropyl ester, melting point 150°–151° C., is obtained from 50 g of N-[1-(5-benzyloxy-indolyl-3-yl)-2-methoxyethyl]-N-isopropylamine(5-benzyloxypseudo-gramine).

EXAMPLE 3

By reaction of 37.02 g of N-[1-(4-benzyloxyindol-3-yl)ethyl]-N-isopropylamine analogously to Example 1, 31.7 g (70.5% of theory) of 5-benzyloxy-4-methyl-β-carboline-3-carboxylic acid isopropyl ester of melting point 190°–191° C. (crystallized from toluene-methanol 1:1) is obtained.

EXAMPLE 4

5.39 g of N-{1-(4-[4-chlorophenyl]-indol-3-yl)methoxymethyl}-N-isopropylamine reacted analogously to Example 1 provides 3.28 g (51.4% of theory) of 5-(4-chlorophenoxy)-4-methoxymethyl-β-carboline-3-carboxylic acid isopropyl ester of melting point 119°–120° C.

EXAMPLE 5

0.72 g of 5-(4-chlorophenoxy)-β-carboline-3-carboxylic acid isopropyl ester of melting point 273°–274° C. (yield 37.9% of A theory) is obtained from 1.57 g of N-{1-(4-[4-chlorophenoxy]-indol-3-yl)-methyl}-N-isopropylamine according to Example 1.

EXAMPLE 6

By condensation of 2-(4-methoxybenzylidine-amino)-acetic acid methyl ester and N-isopropyl-N-[1-(5,6-dimethoxyindol-3-yl)propyl]-amine and further reaction as described in Example 1, 6,7-dimethoxy-4-ethyl-β-carboline-3-carboxylic acid methyl ester of melting point 207°–209° C. (yield 52% of theory) is obtained.

We claim:

1. Process for the production of compounds of formula I

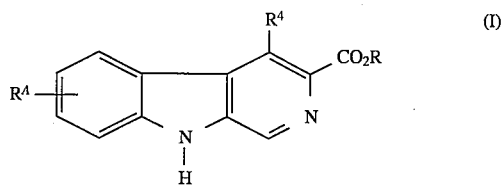

in which $R^A$ means hydrogen, halogen, —$CHR^1$—$R^2$; phenyl, hetaryl or $OR^5$ optionally substituted with halogen, $C_{1-4}$ alkoxy or amino and can be single to double, and $R^1$ means hydrogen or $C_{1-4}$ alkyl, $R^2$ means hydrogen, $C_{1-4}$ alkyl, —O—$C_{1-4}$ alkyl or an optionally substituted phenyl, benzyl or phenoxy radical, and $R^5$ means hydrogen, $C_{1-6}$ alkyl, $C_{3-7}$ cycloalkyl or an optionally substituted phenyl, benzyl, hetaryl or benzo-condensed hetaryl radical, $R^4$ means hydrogen, $C_{1-4}$ alkyl or $C_{1-4}$ alkoxy-$C_{1-2}$ alkyl and R means $C_{1-6}$ alkyl, characterized in that a compound of formula II

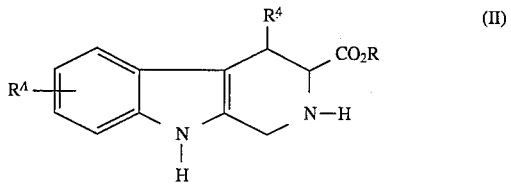

in which

R, $R^A$ and $R^4$ have the above meaning, is aromatized with trichloroisocyanuric acid in the presence of bases.

* * * * *